United States Patent
Jaffal

(10) Patent No.: US 10,407,659 B2
(45) Date of Patent: Sep. 10, 2019

(54) MINI-INCUBATOR CARRIER BOX "MINI-INCUBATOR"

(71) Applicant: Sahar M. H Jaffal, Boston, MA (US)

(72) Inventor: Sahar M. H Jaffal, Boston, MA (US)

( * ) Notice: Subject to any disclaimer, the term of this patent is extended or adjusted under 35 U.S.C. 154(b) by 164 days.

(21) Appl. No.: 15/343,490

(22) Filed: Nov. 4, 2016

(65) Prior Publication Data
US 2017/0127665 A1    May 11, 2017

Related U.S. Application Data

(60) Provisional application No. 62/285,741, filed on Nov. 9, 2015.

(51) Int. Cl.
| | | |
|---|---|---|
| *C12M 1/34* | (2006.01) | |
| *A01N 1/02* | (2006.01) | |
| *C12M 3/00* | (2006.01) | |
| *C12M 1/00* | (2006.01) | |

(52) U.S. Cl.
CPC .......... *C12M 41/40* (2013.01); *A01N 1/0252* (2013.01); *A01N 1/0273* (2013.01); *C12M 23/20* (2013.01); *C12M 23/54* (2013.01); *C12M 41/12* (2013.01); *C12M 41/34* (2013.01); *C12M 45/22* (2013.01)

(58) Field of Classification Search
USPC ............ 435/284.1; 220/560.01, 592.09, 88.1
See application file for complete search history.

(56) References Cited

U.S. PATENT DOCUMENTS

| | | | | |
|---|---|---|---|---|
| 4,470,264 | A  * | 9/1984 | Morris | A01N 1/02 62/372 |
| 6,582,953 | B2 * | 6/2003 | Brasile | A01N 1/02 435/1.2 |
| 7,240,513 | B1 * | 7/2007 | Conforti | A45C 13/02 62/457.2 |
| 8,304,181 | B2 * | 11/2012 | Hassanein | A01N 1/0247 435/1.1 |
| 8,327,659 | B2 * | 12/2012 | Winkler | F25D 3/08 220/592.25 |
| 8,697,430 | B2 * | 4/2014 | Toguchida | A01N 1/0252 435/1.1 |
| 8,835,158 | B2 * | 9/2014 | Judson | A01N 1/0247 435/1.1 |
| 9,301,519 | B2 * | 4/2016 | Hassanein | A01N 1/0247 |

(Continued)

*Primary Examiner* — Nina Bhat

(57) ABSTRACT

The carriers that are available in the market don't maintain all the necessary parameters that are mentioned in the subject matter of this application. Many of them are: 1) Costly 2) Allow the transport of cells for short period of time 3) Are suitable for transporting certain type of cells 4) Don't include control for all the parameters that are required for the experiments 5) Need extra steps that can affect cell/organs and waste the time, efforts and money of the researchers. 6) Limit researchers for using containers with certain sizes and materials. 7) Involve changing the conditions of cell growth such as splitting the cells, freezing, centrifuge them during the process of transporting them. Alternatively, the Mini-incubator carrier box in my invention is an economic transport system and practical. It enables the researchers to fix different containers at different sizes using clamps and screws and to transport the organs/samples/cells in any container for long period of time and long distance under optimized conditions without the need of extra steps/costs.

3 Claims, 13 Drawing Sheets

A diagram for the Mini-incubator carrier box and the parts of it.

(56) References Cited

U.S. PATENT DOCUMENTS

| | | | |
|---|---|---|---|
| 9,426,979 B2* | 8/2016 | Anderson | A01N 1/0247 |
| 2005/0153271 A1* | 7/2005 | Wenrich | A01N 1/02 |
| | | | 435/1.1 |
| 2005/0239190 A1* | 10/2005 | Poo | B65D 81/20 |
| | | | 435/284.1 |
| 2006/0228794 A1* | 10/2006 | Ranoux | A61D 19/022 |
| | | | 435/303.1 |
| 2008/0145919 A1* | 6/2008 | Franklin | A01N 1/02 |
| | | | 435/284.1 |
| 2011/0033916 A1* | 2/2011 | Hutzenlaub | A01N 1/02 |
| | | | 435/284.1 |
| 2013/0161331 A1* | 6/2013 | Pherson | B65D 88/14 |
| | | | 220/560.01 |
| 2014/0051165 A1* | 2/2014 | Young | A01N 1/0273 |
| | | | 435/374 |
| 2015/0069068 A1* | 3/2015 | Hariram | A62C 3/16 |
| | | | 220/560.01 |

* cited by examiner

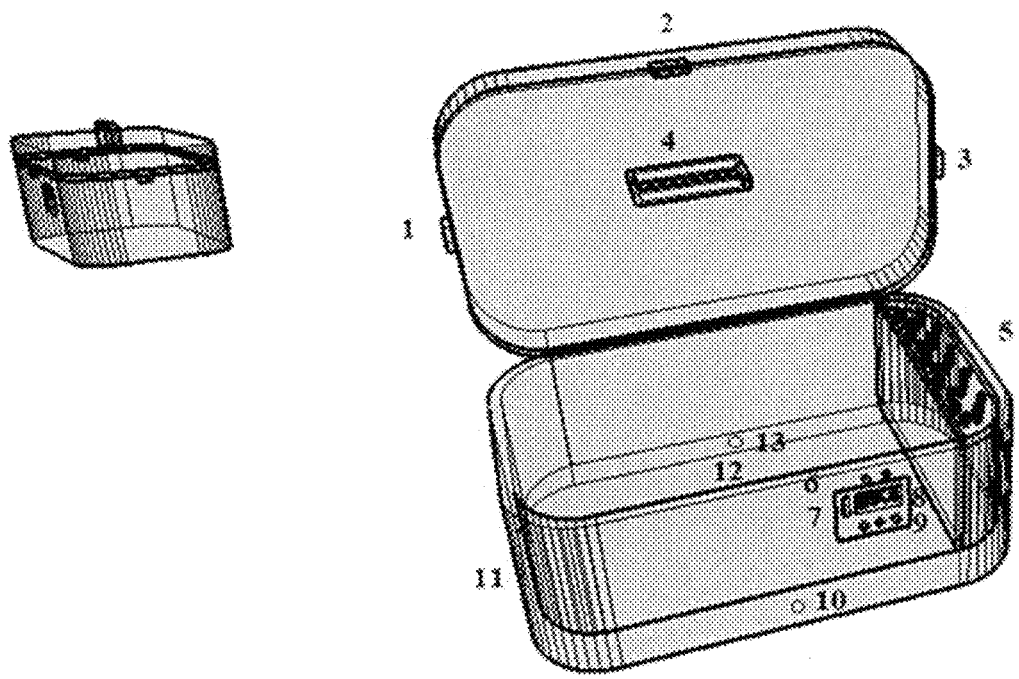
Figure 1: A diagram for the Mini-incubator carrier box and the parts of it.

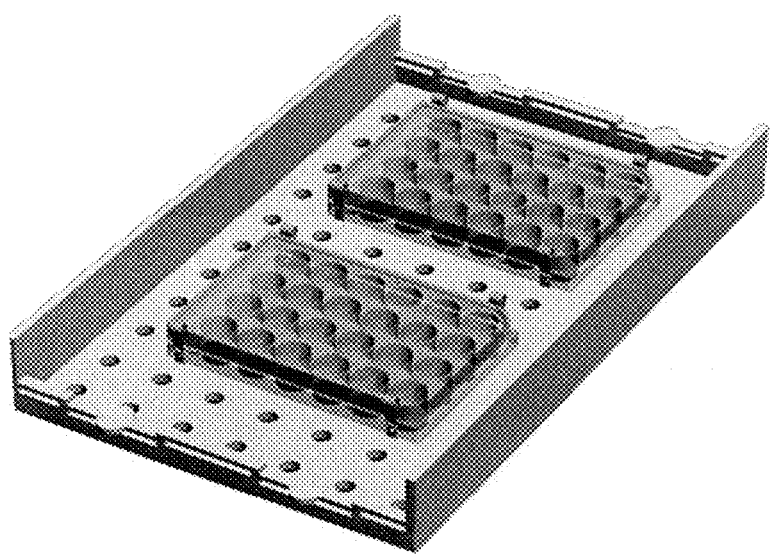
Figure 2: A diagram for the stainless steel tray with a 24 well-plate fixed on top of the tray by clamps.

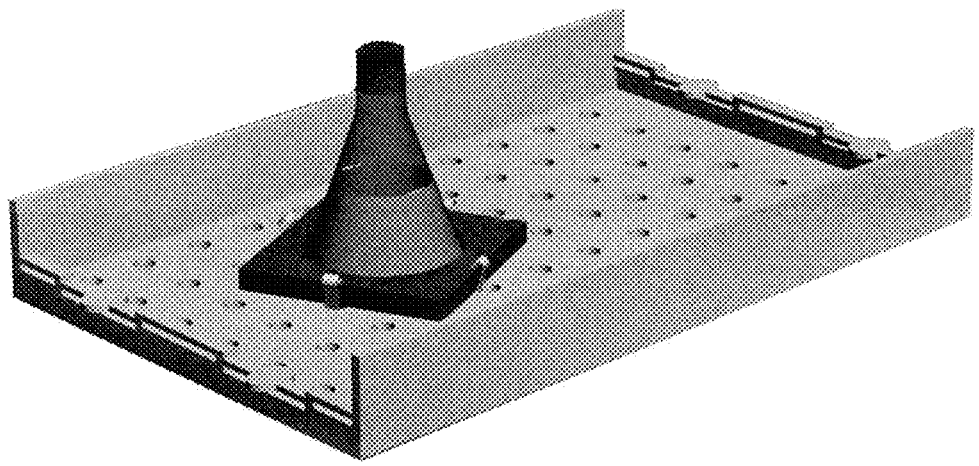
Figure 3: A diagram for the stainless steel tray with an Erlenmeyer flask placed on top of it using an additional flat base that is fixed by clamps on top of the tray.

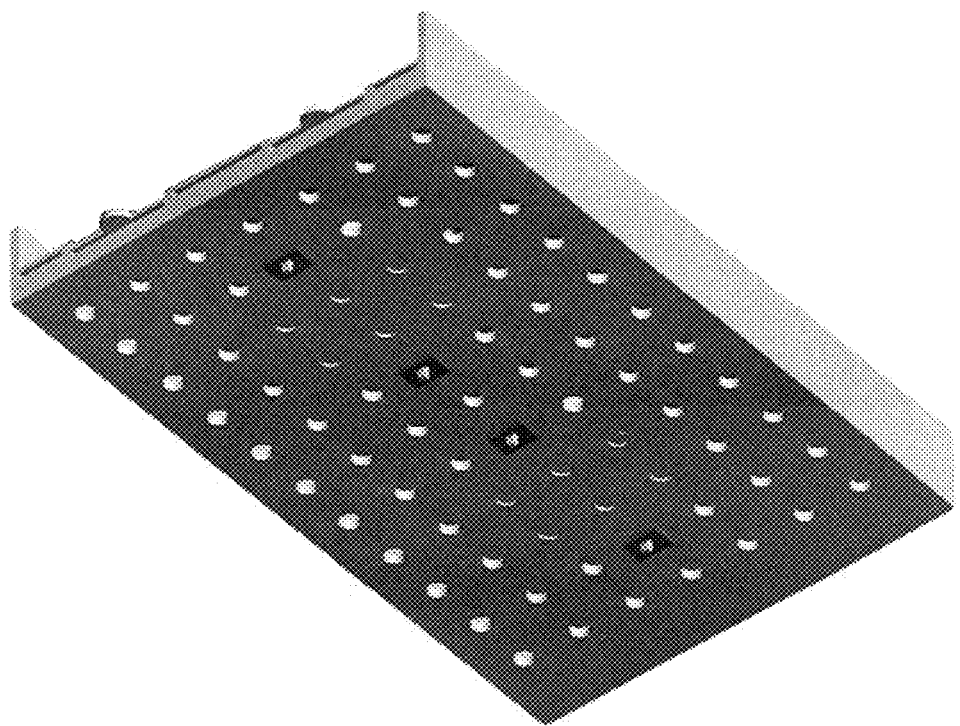
Figure 4: The bottom of the stainless steel tray with clamps that will be connected with screws on the bottom of the tray to fix the container.

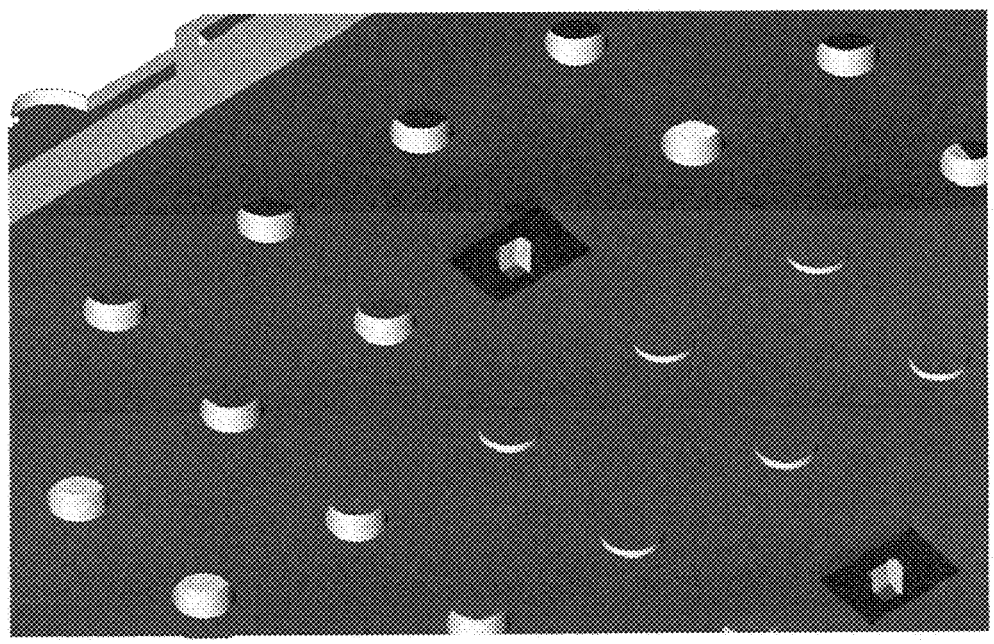
Figure 5: An enlargement of the screws that will be used to fix the clamps in the bottom of the stainless steel tray to hold the container.

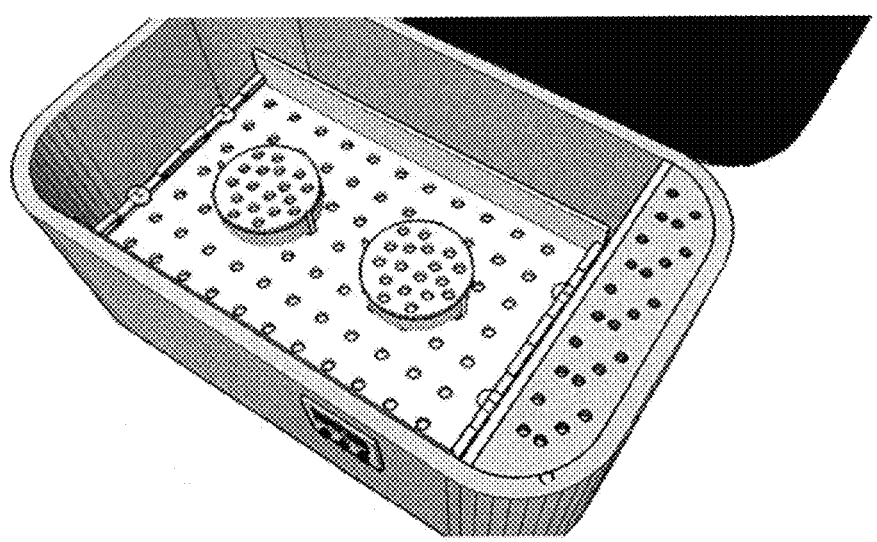
Figure 6: A diagram for the Mini-incubator carrier box with an open lid and 2 Petri-dishes fixed on top of the stainless steel tray.

Figure 7: The design and the shape of the Mini-incubator carrier box in white color (Figure 7A) and black color (Figure 7B).

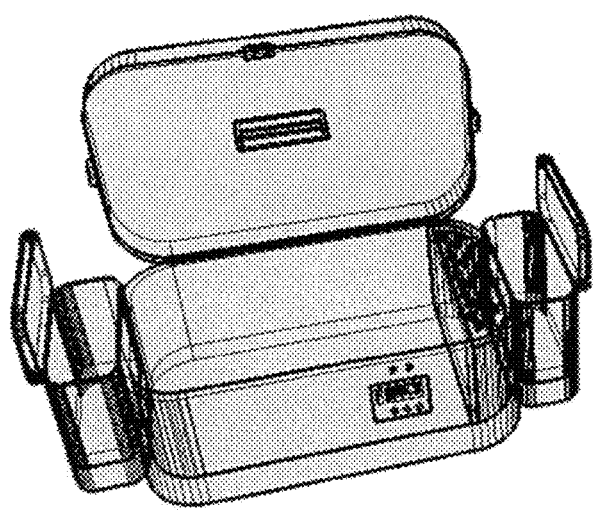
Figure 8: A diagram for the Mini-incubator with a special design (2 additional compartments as a safe storage for the Carbogen gas cylinder and other accessories).

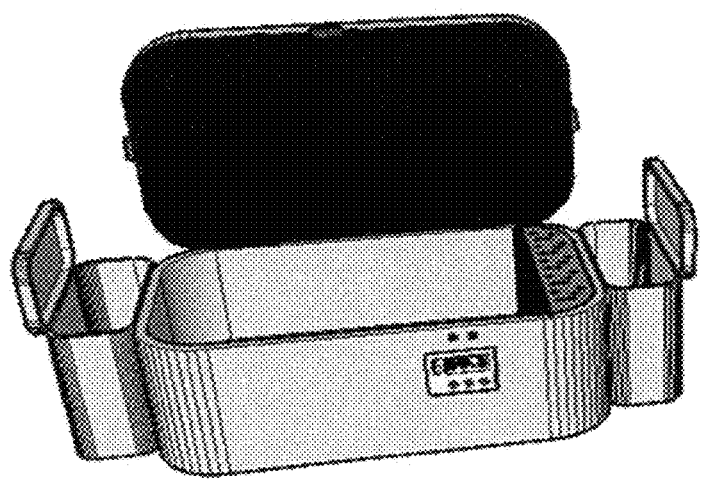
Figure 9: Another diagram for the special design for the Mini-incubator carrier box that is explained in Figure 8.

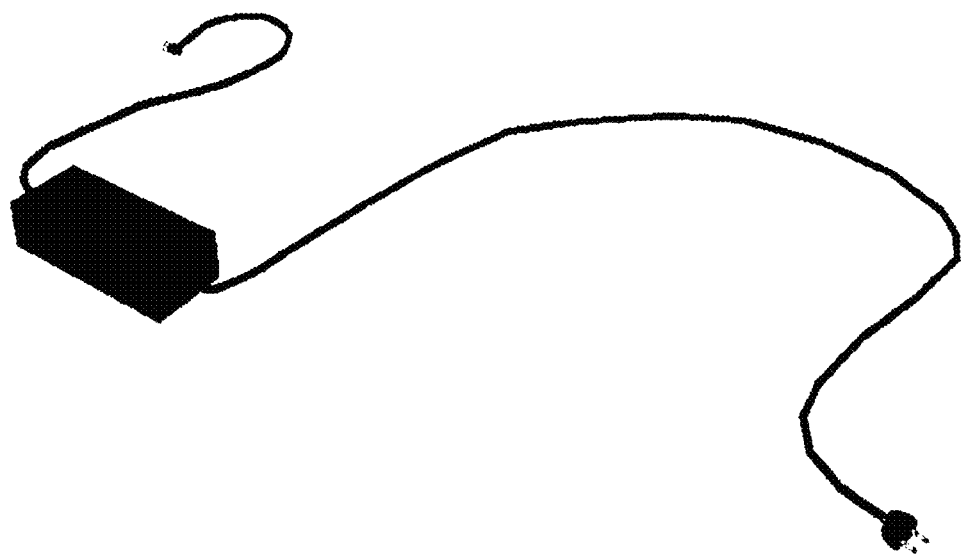
Figure 10: Charger for the battery of the Mini-incubator carrier box.

Figure 11: Carbogen gas cylinder to provide 95% $O_2$ and 5% $CO_2$ in the Mini-incubator carrier box.

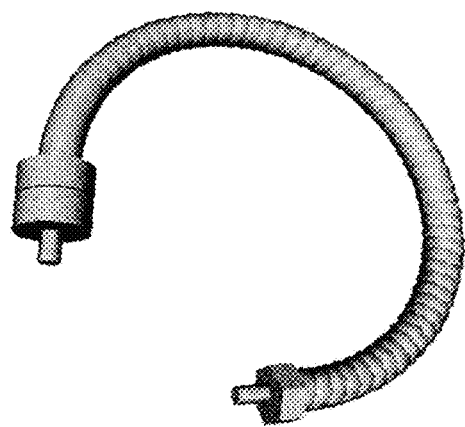
Figure 12: Tube for connecting the gas cylinders to the Mini-incubator carrier box.

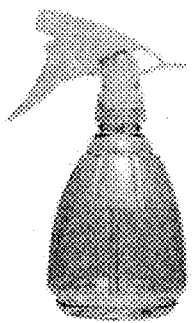
Figure 13: Spray bottle that can be filled with an EPA registered disinfectant to prevent the contamination and infections in the Mini-incubator carrier box.

MINI-INCUBATOR CARRIER BOX "MINI-INCUBATOR"

CROSS-REFERENCE TO RELATED APPLICATION

The application for this invention claims the benefit and priority to the U.S. Provisional Patent Application No. 62/285,741, Filing date: Nov. 9, 2015.

TECHNICAL FIELDS THAT ARE RELATED TO THE INVENTION AND THE PROBLEMS THAT THE INVENTION SOLVES

This invention relates to a Mini-incubator carrier box "Mini-incubator". The invention enables the transport of samples/cells under optimal stabilized conditions and is practical to be used in several fields: Medicine, Cell Biology, Microbiology, Environmental Science, Chemistry, Physics, Geology, Agriculture and other fields.

The Mini-incubator can be, also, used in the hospitals and medical centres for transporting the human organs under stabilized conditions.

BACKGROUND INFORMATION AND PRIOR ART

Maintaining temperature is an important factor that should be taken into consideration during the transport of cells/biological, samples/organs to other places. This is of vital importance in the scientific experiments, medical practices and other fields.

Little changes in the temperature of biological samples and cells can affect the experiment and lead to inaccurate results. If the temperature isn't stable, the obtained results can be attributed to cellular changes occurring from fluctuations in the temperature and not the experimental parameters that the researcher intended to test. However, the results can be reported as experimental results leading to inaccurate conclusion. Changes in the temperature can, also, influence the viability/function of the human organs that are needed in organ transplantation surgeries. Accordingly, a simple change in the temperature can lead to the loss of a lot of money that was spent in research in addition to the waste of the valuable time and efforts of the researcher.

The followings are some examples of the costs that the researcher can lose if errors were conducted in the experiment the cost of buying and culturing cells, the cost of the growth media and the required supplements, the cost of the animals and their housing if primary culture was used, the cost of maintaining the incubator, the cost of the inhibitors, drugs, antibodies, films and membranes, gels of western blot and other materials used in the experiment.

In addition to controlling the temperature, maintaining other conditions is very important for the cells, organs and biological samples. For example, the change in humidity surrounding the samples/cells can increase the concentration of the cell culture media and other solutions by changing the ratio of amino acids, salts and minerals. This change in the growth media can cause toxicity, cell death and inaccurate results that can be reported and analyzed by the researcher as results of the experiment while the results emerged, in fact, from the improper environmental conditions used in the experiment.

The available methods that are used to transport the cells/biological samples are not practical. For example, some scientists wrap the cell flask or the sample container with a blanket, place it inside a styrofoam box and carry the box to another place. Other scientists centrifuge the cells to pellet them or freeze the cells in cryogenic solution to be able transport them for long distance. These methods can affect the cells/biological samples if used repeatedly and aren't effective ways to transport cells and biological samples.

The equipment available in the market aren't practical for transporting biological sample/fixed cells for the following reasons:

A] The lack of the enclosed sterile environment in the styrofoam box/other boxes.

B] The need for the continuous disinfection of the sample container.

C] The lack of control on parameters that are important for maintaining the cells/biological samples including the levels of oxygen ($O_2$), carbon dioxide ($CO_2$) and humidity.

D] Un-suitability of the available methods (e.g. the styrofoam box) for transporting the cells/samples for long distances and long period of time.

E] The use of certain methods (e.g. freezing and thawing the cells) that can affect the contents and the metabolism of the cells and can lead to freezing injury and other effects.

F] Inability to fix the container during the transport of cells and biological samples (restriction in the transport of flasks that contain live cells growing in media).

Erik B Finger referred to the methods that are used in transporting the human organs and organ preservation in the hospitals and the clinics in his article. (http://emedicine.medscape.com/article/431140-overview#a1). The author summarized data from previous studies that included testing the conditions of the organ preservation and the effect of this process on organs. In particular, the author reported that the preservation method disrupts the relation between temperature, osmolality and pH in the cells during cooling the organ (hypothermia).

The author reported that the decrease in temperature affects metabolism in cells. The metabolic rate slows down by a factor of 12-13 when the temperature of the organ decreases from 37° C. (98.6° F.) to 0° C. (32° F.) during the cooling process. It also changes the function of the enzymes that are bound to cell membrane.

OBJECT OF THE INVENTION (THE MINI-INCUBATOR CARRIER BOX) AND THE PROBLEMS THAT THE INVENTION SOLVES

It is almost impossible to find a facility that has all the equipment that are necessary for the scientific research. Some expensive machines are only available in large facilities. As a result, many researchers need to collaborate and share using machines and equipment. Accordingly, the transport of biological samples/cells is a frequent procedure in research and science. This means that researchers face the same problem (the inability to transport live cells and samples under stabilized conditions) all the time and during the whole year.

Despite the fact that the transport of cells/samples outside the building is a challenge for the researchers, the transport of cells/samples inside it is another challenge that the researchers need to pay attention to for the following reasons:

i) The distance of moving the cells from one laboratory to another in the same building can be long.

ii) Even if the distance is short, there can be delays and interruptions during the transport of cells and this can result in keeping cells outside the incubator under unmonitored conditions for longer time.

iii) There is difference in the temperature and other conditions between the rooms in the same building (e.g. due to differences in the heating system, the number of machines in the room, the type of machines in the room, the activities of the people inside the room and other factors). This difference can affect the cells if were transported by styrofoam box.

Sometimes, the effect of keeping the cells under uncontrolled conditions can be noticed. For example, the color of the growth media (with a pH indicator) changes if the culture plate was kept outside the incubator for some time. Even if the effect isn't visible, it doesn't guarantee that no changes occurred to the cells/biological samples during improper transport.

Therefore, manufacturing a properly designed Mini-incubator carrier box solves the previously mentioned problems and enables the researchers to transport cells and samples under sterile and controlled conditions.

On the other hand, organ preservation is an important process due to the narrow time window between harvesting the organ and transplanting the donated organ to the recipient. The process is a critical step that has big impact on preserving the vitality of organs during transport and on saving the lives of many people.

Cells, organs and tissues function effectively only in the range of 36.1° C. (97° F.) to 37.2° C. (99° F.). Hypothermia (low temperature) occurs when heat loss exceeds heat gain and can affect the cells, organs and tissues. Hypertehermia (elevated temperature) can, also, lead to metabolic acidosis, heat shock and other effects.

Accordingly, there is need for a Mini-incubator carrier box that is chargeable, portable, small in size, light in weight and has the features of fixing different containers of samples, organs and cells in liquid media under optimized conditions (humidity, $CO_2$, $O_2$ and temperature).

The advantage of this Mini-incubator carrier box is to allow researchers and clinicians in the hospitals to transport cells/organs/biological samples to different places at different seasons at sterile adjusted optimal conditions (temperature, humidity and levels of $CO_2$ and $O_2$. The design of the Mini-incubator carrier box would also, allow the researchers/clinicians to transport biological samples, cells and organs for long distances (e.g. between provinces or even between countries) and for extended period of time without worrying about changes in the conditions of the surrounding environment and their effects on cells/samples.

The boxes and the carriers that are available in the market don't maintain all the necessary parameters that are mentioned in the Mini-incubator. In particular, these carriers are suitable for transporting certain type of cells. For example, there is a carrier for cell culture that contains a polymer gel layer to maintain the lamination of the cells (U.S. patent application Ser. No.11/099444) without controlling all the parameters that are required for the experiments.

Many inventions are related to carriers that work by using the cooling system or designed to monitor only, one parameter or to transport the samples by suspension in fluids as proposed by Weinmann US2013/0310802.

In US 2010/0196871A1, Dodgson et al. disclosed an apparatus and a method for culturing and/or transporting cellular structures. The apparatus is made up on the principle of enabling gas diffusion to the media. It is mostly useful for transporting embryos and oocytes and doesn't fulfil many of the purposes that are mentioned in the subject matter of this application including the ability to transport different containers at optimized conditions. On the other hand, fewer parameters are controlled in this apparatus compared to the Mini-incubator carrier box.

Additionally, Rapoport et al. (US 2013/0011905) introduced an incubator device. However, this device doesn't solve the problems that are mentioned in this application for the following reasons:

First, Rapoport et al. designed the incubator device and equipped it with a one small cell chamber located inside the incubator device. Accordingly, this design limits the researchers to one size of the cell chamber meaning that researchers need to split the cells using trypsin (or other enzymes) to place them in the chamber before being transported. In fact, researchers need to transport the cells and samples in their original containers (to avoid extra unnecessary steps). If the researcher used the incubator device of Rapoport et al. to transport the cells/samples temporarily then return them back to the first location, the researcher has to split the cells many times. This leads to a waste of time, efforts and money due to the need of using more growth media, supplements of media (e.g. Fetal Bovine Serum, Glutamine, antibiotics . . . etc) and cell containers. The cells will, also, be subject to changes in their conditions. Additionally, this device doesn't enable the researchers to transport cells and the biological samples in their original container.

Second, the design that Rapoport et al. proposed is costly. The size of the cell chamber is very small and doesn't fit transporting large amount/volume of samples.

Third, many researchers, need to transport several containers in the same incubator (when their incubation conditions are similar) to save time, money and effort. These criteria can't be achieved in the invention of Rapoport et al.

Fourth, the type of the material that is used for manufacturing the chambers or containers of cells is a critical factor when the researcher uses microscopes and imaging techniques to image cells that are cultured in their container. Some materials cause a strong background that prevents capturing images with good resolution. This means that the invention of Rapoport et al. isn't suitable for these experiments in which imaging is needed for cells that are cultured alive in specific containers without being split or detached.

Fifth, the design of the incubator device of Rapoport et al. includes a small gas container and allows the transport of cells, mainly, for short period of time (express delivery time). It doesn't solve the problem of the inability of the researchers to transport the cells/samples under optimal conditions.

Practically, the design of the cell chamber in the apparatus of Rapoport et al. limits the transport to certain types of cells. In fact, there are non-adherent cells or some tumour cells that can grow in suspension in special containers coated with specific materials. Accordingly, these kinds of cells can't be transported using the incubator device of Rapoport et al.

Finally, some cells grow very well in certain types of cell flasks or Petri-dishes (manufactured of certain materials) and may not be effectively cultured in the cell chamber of Rapoport et al. In fact, cell flasks or Petri-dishes are not only made of different materials (e.g. glass; plastic), some containers are made of same materials at different percentages (e.g. 26% plastic mixed with other materials. . . . etc) indicating the variety of the available materials that fit different cells.

In summary, the embodiment of Rapoport et al. is relatively costly and isn't tailored to solve the problems that the subject matter of this application is designed to solve.

The Mini-incubator carrier box that is proposed in this application is an economic multi-purpose transport system that can be used for transporting human organs, biological samples or cells in their original containers (cell flasks, Petri-dishes, well-plates, suspended in tube or a beaker) in a cost-effective manner and without the need of extra steps. The screws and clamps that are available in the Mini-incubator carrier box enable fixing different containers for the proper transport of cells. It also enables the researchers to transport the cells/organs for long period of time and long distances under optimized conditions ($CO_2$, $O_2$, humidity and temperature) without the need of extra steps/costs.

BRIEF DESCRIPTION OF THE DESIGN OF THE MINI-INCUBATOR CARRIER BOX AND THE RELATED DRAWINGS

The incubator is an enclosed bassinet that has a hollow cavity and is used to keep the cells/samples in a sterile and stabilized environment to prevent contamination and the growth of microorganisms.

The idea of this invention is to design a special portable chargeable Mini-incubator carrier box that is small in size, light in weight and cost effective for transporting all kinds of live cells and biological samples in fixed containers for long distances and long period of time under sterile monitored conditions in an affordable and convenient way. The box would be useful in research laboratories and hospitals.

FIG. 1 displays a diagram for the Mini-incubator carrier box while FIG. 6 illustrates a diagram for the Mini-incubator carrier box with open lid. The configuration and the design of the Mini-incubator carrier box are shown in FIG. 7.

In order to achieve the above mentioned goals, several characteristics need to be provided as described in the following paragraphs:

The Mini-incubator carrier box would be manufactured using a fireproof and waterproof inert material. The Mini-incubator carrier box would be designed with a lid to close the box. The sealing of the box should be proper to isolate the internal environment of the box from the external environment. This can be achieved using 3 clips or locks to close the box properly (Parts Number 1, 2 and 3 in FIG. 1 illustrate the places of 3 clips that are used to close the Mini-incubator carrier box tightly in order to isolate the internal environment of the box and keep it sterile).

The Mini-incubator carrier box is designed with a handle on the lid so that the user can carry the box easily (Number 4 of FIG. 1). In addition, the Mini-incubator carrier box would be set up with HEPA filtration to capture volatile organic chemicals (VOCs) that can induce stress proteins and cause heat shock to the cells. Also, the design would include 2 switch buttons; a power switch and a fan switch (Number 6 of FIG. 1).

The Mini-incubator carrier box would be arranged to work with a battery that can be charged using a charger or adapter so that the researcher can transport the box easily. The battery can be charged using an electrical plug (FIG. 10 and Number 13 in FIG. 1) or by using a separate portable charger. The battery, would be placed in a waterproof compartment to ensure a safety design for the Mini-incubator.

The Mini-incubator carrier box would be equipped with an indicator for the charge level of the battery. The charge level would be displayed in a digital screen located outside the Mini-incubator carrier box (Number 8 in FIG. 1).

One of the most important aspects in the Mini-incubator carrier box is to design a safe system for filling gases (e.g. $CO_2/O_2$). Number 12 in FIG. 1 is the gas ($CO_2/O_2$) container. The gas container would be placed in an insulated compartment that is securely placed between 2 layers. The gas would be filled using the necessary connecting tube and the Carbogen gas cylinder to provide 95% $O_2$ and 5% $CO_2$ (FIGS. 11 and 12). The connecting tube would be used to connect the Carbogen gas cylinder to the Mini-incubator to inject the $CO_2/O_2$ mixture through the inlet nozzle (Number 10 in FIG. 1). The connecting tube and the small Carbogen gas cylinder are small in size and are part of the design of the Mini-incubator. They would be placed in certain compartments and would be portable.

The Mini-incubator carrier box would be equipped with an outlet pressure gauge that reads the pressure outlet of the gases and a pressure gauge that reads the gas pressure inside the Mini-incubator carrier box.

The size of the container and the amount of $CO_2/O_2$ that can be injected in the Mini-incubator carrier box would be calculated as a percentage using an equation that correlates the size of the standard incubator in the laboratory, the shelf life of the Carbogen gas cylinder needed for the standard incubator and the size of the gas cylinder. Accordingly, the approximate time needed for re-filling the gas in the Mini-incubator carrier box would be calculated in advance and would be provided to the researchers to enable the effective transport of biological samples/cells without exhausting gases from the Mini-incubator.

The Mini-incubator carrier box would be designed with an outlet nozzle to enable the air outlet and the outlet of the pressure/gases during, the transport of cells/samples for long period of time (Number 11 in FIG. 1). Despite the fact that most samples and cells require using $CO_2$ and $O_2$, the Mini-incubator carrier box would be suitable for filling any gas according to the requirements of the experiments.

The design of the Mini-incubator carrier box includes a digital screen that shows the readout of different parameters in the box. The screen would work as a readout display for the temperature, humidity and the levels of the $CO_2/O_2$. The screen would also display the charge level of the battery and an alarm sign if one or more of the parameters deviated from the adjusted required level (Number 8 in FIG. 1).

The Mini-incubator carrier box has 3 knobs (below the digital screen) that would allow the researcher to adjust the temperature, humidity and the level of the $CO_2/O_2$ inside the Mini-incubator carrier box according to the requirements of the experiment (Number 9 of FIG. 1).

Two buttons (⇕) can be used to increase or decrease the values of different parameters according to the required conditions that are suitable for the cells/samples (Number 7 of FIG. 1).

The internal side of the Mini-incubator carrier box would be made of stainless steel (rust proofing) to avoid the corrosion of the material by the humidity.

The Mini-incubator carrier box would include water reservoir with perforated cover. Water reservoir would be used to humidify the air inside the box (Number 5 in FIG. 1). Sterile distilled water should be used to fill the water reservoir.

The design of the Mini-incubator carrier box would include a control unit with sensors to maintain the parameters at fixed readings. This is very important because little change in any parameter can affect other conditions in the box. For example, a change in humidity can damage gas sensors.

Different sensors would be, also, available in the Mini-incubator carrier box. For example, temperature sensors including thermostat that controls the temperature and prompts the system to reach the desired temperature and thermometer that measures changes in the temperature and displays the actual temperature of the Mini-incubator. Other sensors include humidity sensor and pressure sensor. The incubator would also include $CO_2$ flowmeter/$O_2$ flowmeter to check the flow of gases.

The Mini-incubator carrier box would include hot cycle pump that circulates heat in the box. It would, also, include a fan (natural flow air) that circulates air in the incubator.

The heating control system (or temperature control mode) is designed to respond to changes that are detected by the sensor when there is difference between the actual temperature and the required temperature. This system provides electrical power to the heating coil to adjust the temperature.

The plate or the container of the cells/samples would be fixed by clamps. The clamps would be used to hold the container of the cells/biological samples on a stainless steel tray inside the Mini-incubator carrier box through screws used to fix the clamps to the bottom of the tray. FIG. 2 shows a 24 well-plate used for culturing cells. The 24 well-plate is fixed on the stainless steel tray using clamps and screws (FIGS. 4 and 5).

If the researcher wants to transport an Erlenmeyer flask or other big laboratory container, the container would be placed on the stainless steel tray using an additional flat base that would be fixed by clamps on top of the tray and by screws to the bottom of the tray. The aim of using the base is to give a strong hold and fixation to this container and to prevent its movement during transport (FIG. 3).

The Mini-incubator carrier box can be designed at different sizes meaning that the researcher can choose a design with several stainless steel trays placed on top of each other (separated by a adjustable distance) and can transport many samples at the same time. This design can save money, time and effort.

The Mini-incubator carrier box can be designed with the option of using a rotator, stirrer, shaker or a cooling system for the samples. In case of choosing a design with a shaker, the Mini-incubator would have additional features (e.g. increasing the number of the outlet nozzles to decrease the internal heat that is generated from shaking).

Furthermore, different kinds of stainless steel trays would be designed to fit different samples. The trays and other accessories of the Mini-incubator carrier box can be provided separately. Some stainless steel trays would be made up to fit Eppendorf tubes (e.g. 1.5 ml, 2 ml, 5 ml), PCR tubes and different vials. Other stainless steel trays would be designed to fit one of the followings: different sizes of centrifuge tubes (e.g. 15 ml or 50 ml tubes), different sizes of Petri-dishes, cell flasks, different well-plates (e.g. 24 well-plate, 48 well-plate, 96 well-plate), cryogenic vials, ultracentrifuge tubes, Erlenmeyer flasks and beakers.

In addition, the researcher can request a custom design for a mixed stainless steel tray to use it for holding different containers in the same tray and at the same time. For example, a tray that contains holding places for Eppendorf tubes, centrifuge tubes, flasks or other containers can be used. This would allow the researcher to transport many samples and cells cultured in different containers in one box (when the required conditions are similar) and can save the researcher time, money and effort. The Mini-incubator carrier box would be designed in attractive way with different colors and/or scientific pictures printed on the box (like DNA or Neurons . . . etc) so that the box appears as scientific box.

The Mini-incubator carrier box would have another design (FIGS. 8 and 9) that allows the researcher to transport the samples/cells/organs for long distance and when the needed time for the transport exceeds the calculated time for the shelf life of the gas in the Mini-incubator carrier box. Accordingly, it helps in broadening the time window of transporting the cells/samples by the researcher.

The design (as it appears in FIGS. 8 and 9) includes extra compartments outside of the box for the safe storage of the Carbogen gas cylinder (FIG. 11) and other parts of the Mini-incubator carrier box such as the connecting tubes and the spray bottle of a disinfectant as shown in FIGS. 12 and 13. The disinfectant would be EPA (US Environmental Protection Agency)-registered such as quaternary ammonium disinfectant. The researcher can use the disinfectant on a regular basis to prevent the contamination inside the box and has to sterilize the Mini-incubator carrier box once every week or every two weeks by using sterilization gases such as ozone and hydrogen peroxide gas.

Due to the importance of having a stabilized environment for the biological samples and live cells under different conditions, my idea is to broaden the range of adjusted parameters in the box including the temperature. New features that give the researchers the choice of transporting samples at cold temperature or warm temperature would be added to the design. As a result, the researcher can transport any item in the laboratory in a small box regardless of the storage conditions. Samples that need to be stored at room temperature, in the fridge, in the freezer, at −80° C. or liquid nitrogen can be transported in this box. This design would allow the researcher to have a portable multi-purpose carrier box that can work as one or more of the followings: an incubator, fridge, freezer or as a liquid nitrogen storage container.

LIST OF FIGURES AND DRAWINGS

FIG. 1 displays a diagram for the Mini-incubator carrier box and the parts of this box as the following: Number 1, 2 and 3 are the places of 3 clips; Number 4 is the handle of the Mini-incubator carrier box; Number 5 is the water reservoir, Number 6 shows the power switch and the fan switch; Number 7 is the place of the 2 buttons that are used to adjust the readings in the Mini-incubator carrier box; Number 8 is the digital screen; Number 9 is the place of 3 knobs to control the temperature, humidity and the levels of $CO_2/O_2$; Number 10 is an inlet nozzle for the infecting $CO_2/O_2$; Number 11 is an outlet nozzle; Number 12 is the $CO_2/O_2$ container; Number 13 is a hole for the plug of the charger.

FIG. 2 shows a diagram for the stainless steel tray with a 24 well-plate fixed on top of the tray by clamps. Number 1, 2, 3 and 4 are the places of 4 clamps; Number 5 is a 24 well-plate; Number 6 is a stainless steel tray.

FIG. 3 illustrates a diagram for the stainless steel tray with an Erlenmeyer flask placed on top of it using an additional flat base that is fixed by clamps on top of the tray in order to give a strong hold and fixation to large laboratory wares (e.g. flasks). Number 1, 2, 3 and 4 are the places of 4 clamps that fix the base to the stainless steel tray; Number 5 is a base; Number 6 is an Erlenmeyer flask.

FIG. 4 illustrates a bottom of the stainless steel tray. The tray would be used to fix the container of the cells/biological samples on top of it by clamps that would be connected with screws on the bottom of the tray.

FIG. 5 shows an enlargement of the screws that would be used to fix the clamps to the bottom of the stainless steel tray for proper holding of the plate or the container of the cells/biological samples.

FIG. 6 illustrates a diagram for the Mini-incubator carrier box with an open lid showing that the inside of the box is made of stainless steel. It shows 2 Petri-dishes fixed on top of the stainless steel tray by clamps.

Figure 7A:
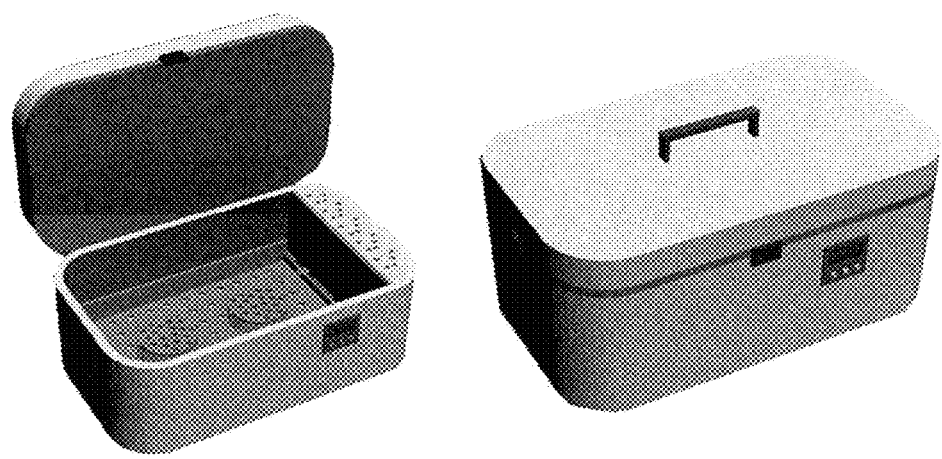
Figure 7B:
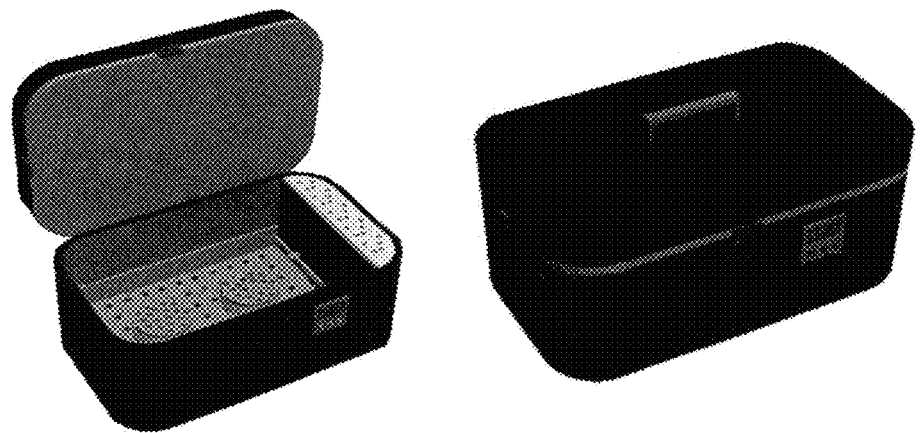

FIG. 7: The design and the shape of the Mini-incubator carrier box in white color (FIG. 7A) and black color (FIG. 7B).

FIG. 8 displays a special diagram for the Mini-incubator carrier box with a special design in which 2 additional compartments are added to the outside of the box as safe storage for the Carbogen gas cylinder and other accessories of the Mini-incubator carrier box such as connecting tube and spray bottle of an EPA-registered disinfectant. The design allows the researcher to transport the samples/cells/organs for long distance and when the needed time for the transport exceeds the shelf life of the gas in the Mini-incubator carrier box.

FIG. 9 displays another diagram for the special design of the Mini-incubator carrier box that is explained in FIG. 8.

FIG. 10: Charger for the battery of the Mini-incubator carrier box.

FIG. 11: Carbogen gas cylinder to provide 95% $O_2$ and 5% $CO_2$ in the Mini-incubator carrier box.

FIG. 12: Tube for connecting the gas cylinder to the Mini-incubator carrier box.

FIG. 13: Spray bottle that can be filled with the disinfectant to prevent contamination in the Mini-incubator carrier box.

The invention claimed is:

1. A portable mini-incubator carrier box for transporting biological samples and live cells comprising:
    an incubating carrier box for housing said biological samples and live cells;
    in operative connection with said carrier box are temperature sensing and adjustable controllers for maintaining temperature, humidity and carbon dioxide and oxygen gas levels within the carrier box;
    an inlet nozzles in operative connection with said incubating carrier box for introducing a carbon dioxide and oxygen into said incubating carrier box;
    an outlet nozzles in operative connection for removing gases from said incubating carrier box;
    a portable carbogen gas cylinder for introducing carbon dioxide and oxygen, wherein a mixture of gases of 95% oxygen and 5% carbon dioxide is in operative connection with said incubating carrier box;
    disposed within the said carrier box includes rustproof stainless steel trays, clamps and screws for fixing and retaining containers;
    a handle on the exterior of said carrier box for carrying and transporting said incubating carrier box;
    a power source, battery and charging mechanism for providing power to said incubating carrier box;
    a digital screen used for displaying the temperature, pressure and gas levels for maintaining said incubating carrier box;
    wherein said incubating carrier box is constructed of materials which are fireproof and waterproof.

2. The portable mini-incubator carrier box of claim 1, wherein said rustproof stainless steel trays are in operative connection with a shaking or stirring device located at the base of the carrier box for rotating and shaking said trays optionally actuated by buttons located outside of said portable mini-incubator carrier box.

3. The portable mini-incubator carrier box of claim 1 wherein said incubator carrier box further comprises thermally controlled heating and cooling units configured to be disposed at the base of said portable mini-incubator carrier box controlled by actuating buttons located outside of said portable mini-incubator carrier box.

* * * * *